United States Patent [19]

Lee et al.

[11] Patent Number: 4,559,109
[45] Date of Patent: Dec. 17, 1985

[54] DEHYDRATION OF ALCOHOL WITH EXTRACTIVE DISTILLATION

[75] Inventors: Fu-Ming Lee; Robert H. Pahl, both of Bartlesville, Okla.

[73] Assignee: Phillips Petroleum Company, Bartlesville, Okla.

[21] Appl. No.: 480,999

[22] Filed: Mar. 31, 1983

[51] Int. Cl.$^4$ .............................................. B01D 3/40
[52] U.S. Cl. ........................................ 203/19; 203/51; 203/56; 203/57; 203/58; 203/64; 203/75; 203/82; 203/DIG. 13; 435/161
[58] Field of Search ............ 203/19, 81, 82, DIG. 13, 203/18, 74, 75, 51, 56, 57, 58, 63, 64, 12–17; 426/494; 435/161; 44/56; 568/916, 918; 202/154

[56] References Cited

U.S. PATENT DOCUMENTS

| | | | |
|---|---|---|---|
| 2,017,067 | 10/1935 | Kraft | 203/19 |
| 2,350,256 | 5/1944 | Shiras et al. | 203/17 |
| 2,542,454 | 2/1951 | Arnold et al. | 518/724 |
| 2,591,671 | 4/1952 | Catterall | 203/18 |
| 2,721,170 | 10/1955 | Johnson | 203/81 |
| 2,775,627 | 12/1956 | Lavender | 203/81 |
| 2,901,404 | 8/1959 | Kirshenbaum et al. | 203/12 |
| 2,922,753 | 1/1960 | Nelson | 203/82 |
| 3,445,381 | 5/1969 | De Graff et al. | 208/313 |
| 3,464,896 | 9/1969 | Washall | 203/18 |
| 3,575,818 | 4/1971 | West | 203/19 |
| 3,955,939 | 5/1976 | Sommer et al. | 203/18 |
| 4,239,926 | 12/1980 | Grane et al. | 203/18 |
| 4,306,884 | 12/1981 | Roth | 44/56 |
| 4,362,601 | 12/1982 | Morita | 203/19 |
| 4,366,032 | 12/1982 | Mikitenko et al. | 203/19 |
| 4,400,241 | 8/1983 | Braithwaite et al. | 203/19 |

OTHER PUBLICATIONS

M. R. Ladisch and K. Dyck, "Dehydration of Ethanol: New Approach Gives Positive Energy Balance," *Science*, vol. 205, Aug. 31, 1979, pp. 898–900.

*Primary Examiner*—Wilbur Bascomb
*Attorney, Agent, or Firm*—French & Doescher

[57] ABSTRACT

A process for producing anhydrous ethanol from an ethanol-water mixture feedstock comprising subjecting the feedstock to distillation in a first distillation zone to produce an overhead vapor of from about 80 to about 90 weight percent ethanol, subjecting the thus produced overhead vapor to extractive distillation in an extractive distillation zone to produce anhydrous ethanol vapor overhead of about 99.5 weight percent ethanol and a solvent-rich bottom stream, and stripping the solvent-rich bottom stream and recycling the thus produced lean solvent bottom stream to the extractive distillation zone and recycling the thus produced overhead vapor stream to the first distillation zone. Also disclosed is a system for performing the process.

15 Claims, 6 Drawing Figures

DEHYDRATION OF ALCOHOL WITH EXTRACTIVE DISTILLATION

This invention relates generally to the processing of alcohol. In one aspect the invention relates to a process for the dehydration of a mixture comprising ethanol and water. In another aspect the invention relates to apparatus for dehydrating a mixture comprising water and ethanol. More specifically, but not by way of limitation, the invention relates to a novel combination of ordinary distillation and extractive distillation utilizing a selective solvent to recover anhydrous ethanol from feedstocks such as fermentation broths containing low concentrations of ethanol.

Typically, effluents from fermentation processes contain alcohol concentrations in the range from about 6 to about 13 weight percent based on the total weight of the effluent, such concentration depending on the material or materials being fermented. The concentration of alcohol from such aqueous solutions is probably the earliest application of distillation since mankind developed an interest in alcoholic beverages long before chemistry or engineering were defined as science or skill.

Recovery of alcohol of high concentration from aqueous solutions by distillation is hampered by the alcohol-water azeotrope which is about 95.6 weight percent ethanol. This azeotrope can be broken by the addition of a third component, such as an organic solvent or a strong salt. Both such distillations require a large amount of energy as well as a third separation step which is necessary for stripping water from the solvent or salt.

It has been shown by M. R. Ladisch and K. Dyck, in "Dehydration of Ethanol: New Approach Gives Positive Energy Balance", *Science*, Vol. 205, Aug. 31, 1979, pages 898–900, that the energy required for the initial distillation of an aqueous solution of 12 weight percent ethanol escalates sharply as the product concentration exceeds the 85–90 weight percent range. As the product concentration approaches the azeotropic composition (about 95.6 weight percent ethanol) the energy required for the distillation approaches the heat of combustion of the product ethanol, and the energy efficiency of such a process approaches zero.

The present invention contemplates an integrated process in which the initial distillation ultimately rejects all the water removed in the process as kettle product, and ethanol is concentrated to no more than about 90 weight percent as the overhead product. This overhead product is yielded from the initial distillation step as a vapor and becomes the vapor feed to an extractive distillation step wherein the vapor is contacted with a selective solvent to remove the remaining water from the ethanol. Solvents which can be advantageously employed include glycols such as ethylene glycol, diethylene glycol, trimethylene glycol, triethylene glycol, and tetraethylene glycol, glycerin, sulfolane, N-methyl pyrrolidone, phenylthioethanol, di-n-propyl sulfone and 1,4-butanediol, the most advantageous solvents being glycerin and ethylene glycol. Rich solvent from the solvent extractive distillation step passes to the solvent stripper from which the vaporous overhead product is injected into the fractionator at a suitable intermediate point and the lean solvent is returned to the extractive distillation column.

It is an object of the present invention to improve the efficiency of production of anhydrous ethanol.

A further object of the invention is to provide an efficient and economical process for the production of anhydrous ethanol from fermentation broth effluents from fermentation processes.

Another object of the invention is to provide a process for the production of anhydrous ethanol having reduced energy requirements.

Yet another object of the present invention is to increase the energy efficiency of a distillation process for the production of anhydrous ethanol.

Still another object of the present invention is to provide a system for the efficient production of anhydrous ethanol.

A further object of the present invention is to provide method and apparatus for the production of anhydrous ethanol which are simple, efficient and reliable.

Other aspects, features, advantages and objects of the present invention will be apparent from the detailed description of the invention, the appended claims and the accompanying drawing in which:

Figure 1:
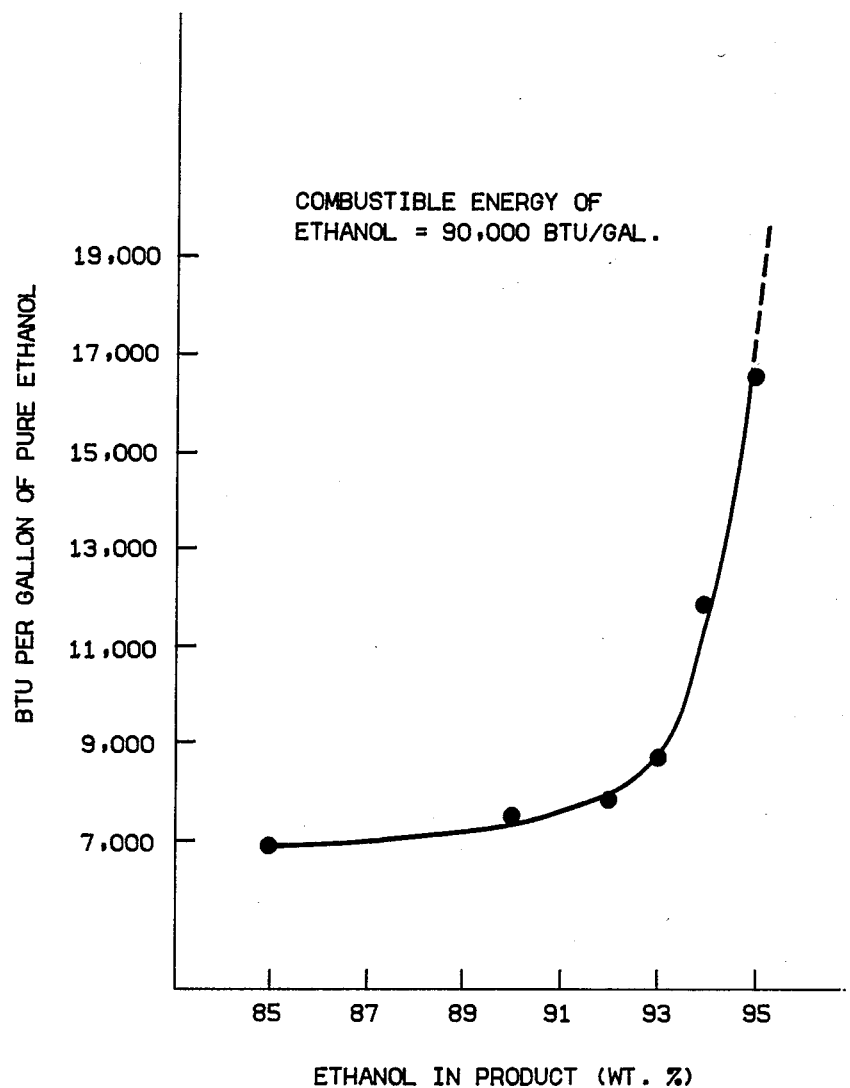
FIG. 1 is a graphical representation of the distillation energy required to produce ethanol of a concentration of from 85 to 95+ weight percent from a starting ethanol concentration of 12 weight percent.

A conventional method for recovering anhydrous ethanol from an aqueous alcohol solution such as a fermentation broth is at least a three-step process. Such a process generally comprises the steps of distillation of dilute aqueous ethanol to its azeotrope (about 95.57 weight percent ethanol), azeotropic distillation using a third component to break up the azeotrope and remove the remaining water; and distillation to separate water from the third component so that the third component can be recycled. Such a method consumes 50 to 80 percent of the energy used in a typical fermentation ethanol manufacturing process, and is frequently cited in criticizing the potential of biomass-derived ethanol as a liquid fuel, as is mentioned by Ladisch and Dyck in their article mentioned above. Most of the energy consumption occurs in distilling above 85 percent ethanol. With increasing ethanol product concentration, the rectifying operating line approaches the equilibrium line and requires more theoretical plates in the distillation column to produce high purity ethanol. To minimize the number of theoretical plates, a higher reflux ratio is required. Thus the energy input requirement becomes larger. As shown in FIG. 1, the incremental energy requirement to produce ethanol of 90 weight percent or higher purity increases precipitously. When the azeotrope is approached, the distillation energy input approaches the ethanol energy output. Additional energy is required to carry out other distillations needed to break the azeotrope.

Figure 2:
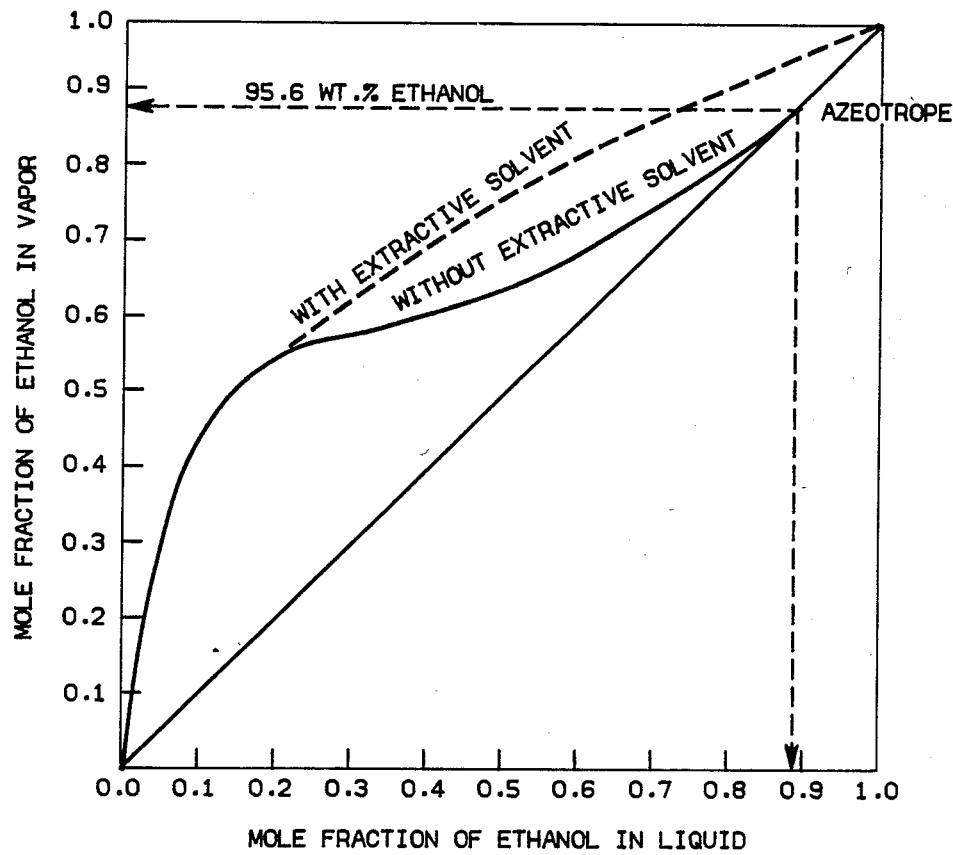
FIG. 2 is a graphical representation of the vapor-liquid equilibrium (VLE) relationships of an ethanol-water system.

In accordance with this invention, extractive distillation solvents have been developed which eliminate the ethanol-water azeotrope and change the shape of the ethanol-rich vapor-liquid equilibrium (VLE) curve into an excellent curve for distillation as shown in FIG. 2. An energy-saving extractive distillation process for producing anhydrous ethanol in accordance with the present invention is based on data developed in the investigation of such extractive distillation solvents. As used herein the term anhydrous ethanol broadly includes a product comprising greater than 95.57 weight percent ethanol, preferably comprising at least about 99 weight percent ethanol, and most preferably comprising at least about 99.5 weight percent ethanol, based on the total weight of the product.

The selection of extractive distillation solvents involves the screening of numerous solvents to determine their effectiveness in aiding the separation of the key components. The problem of estimating effectiveness of solvents is basically a matter of estimating activity coefficients of the solutes in the presence of the solvents.

In recent years, many theoretical and empirical approaches to solution behavior have been advanced which permit the preliminary estimation of activity coefficients in some mixtures. However, the behavior of solutions is far from being fully understood. Experimentation on actual mixtures is still a widely used method for solvent screening, especially for the strong polar mixtures such as ethanol-water-glycols.

The following example describes a method by which solvents are screened in accordance with the present invention.

EXAMPLE I

In this example solvent screening was performed using a vapor-liquid Othmer-type equilibrium still. The capacity of the still was about 500 mL with a heated vapor-rising space in the upper portion thereof. The still was also equipped with a liquid thermowell and a vapor thermowell for obtaining temperature measurements respectively in the liquid and vapor within the still. An ethanol-water mixture containing 99 weight percent ethanol based on the total weight of the mixture was mixed with a known amount of each solvent being screened and from about 100 to about 200 mL of the resulting final mixture was fed into the still. During each run, the liquid portion of the still was completely submerged in a constant temperature bath where the temperature was controlled within $\pm 0.2°$ F. The temperature of the vapor-rising space within the still was maintained at a few °F. higher than the temperature of the liquid portion of the still to prevent partial condensation of the vapor on the inner walls of the vapor-rising space. The temperature of the vapor-rising space was so maintained by means of electric heating tapes disposed about the outer surface of the still surrounding the vapor rising space. Liquid mixing in the liquid portion of the still was provided by a magnetic stirrer. The control temperature of the liquid portion of the still was maintained at temperatures in the range from about 182° F. (83° C.) to about 239° F. (115° C.).

After the whole system reached equilibrium in each run, a sample of about 0.5 mL of vapor condensate was removed from a vapor condensate reservoir in the upper portion of the still via a septum, and the sample was subjected to analysis. For each successive run, a known amount of water was added to the still to change the liquid composition of the ethanol-water mixture. This procedure was repeated in the evaluation of each solvent until the ethanol concentration in the still reached about 50 weight percent on a solvent-free basis.

For each run, the relative volatility of ethanol to water ($\alpha_{12}$) was calculated from the observed data, according to the following equation:

$$\alpha_{12} = (Y_1/X_1)/(Y_2/X_2)$$

where $X_1$ and $X_2$ are mole fractions of ethanol and water, respectively, in the liquid phase, and $Y_1$ and $Y_2$ are the mole fractions of ethanol and water, respectively, in the vapor phase. All compositions were measured or calculated on a solvent-free basis.

Eleven different solvents were evaluated at various temperatures, ethanol-water compositions and solvent to ethanol-water ratios (S/F). The temperature and pressure conditions, weight percent ethanol in liquid, weight percent water in liquid, weight percent ethanol in vapor, weight percent water in vapor, mole fraction ethanol in liquid, mole fraction ethanol in vapor, calculated solvent to ethanol-water weight ratio, and calculated relative volatility ($\alpha_{12}$) for the various solvents are presented in Tables I through XI.

TABLE I

| | | | EQUILIBRIUM DATA FOR ETHANOL-WATER-TETRAETHYLENE GLYCOL MIXTURES | | | | | | |
|---|---|---|---|---|---|---|---|---|---|
| Run No. | Temp (°F.) | Wt. % Ethanol in Liquid | Wt. % $H_2O$ in Liquid | Wt. % Ethanol in Vapor | Wt. % $H_2O$ in Vapor | M.F. Ethanol in Liquid | M.F. Ethanol in Vapor | Solvent to Ethanol-$H_2O$ Wt. Ratio | Relative Volatility ($\alpha$-ethanol/$H_2O$) |
| 1 | 207 | 99.05 | 0.95 | 99.59 | 0.41 | 0.976 | 0.990 | 3.5 | 2.33 |
| 2 | 207 | 97.96 | 2.04 | 99.39 | 0.61 | 0.949 | 0.985 | 3.5 | 3.39 |
| 3 | 207 | 94.48 | 5.52 | 97.61 | 2.39 | 0.870 | 0.941 | 3.4 | 2.39 |
| 4 | 205 | 89.56 | 10.44 | 95.46 | 4.54 | 0.770 | 0.891 | 3.3 | 2.45 |
| 5 | 203 | 82.40 | 17.60 | 92.63 | 7.37 | 0.647 | 0.831 | 3.0 | 2.68 |
| 6 | 202 | 76.11 | 23.89 | 89.92 | 10.08 | 0.555 | 0.777 | 2.8 | 2.80 |
| 7 | 200 | 66.48 | 33.52 | 85.68 | 14.32 | 0.437 | 0.700 | 2.5 | 3.02 |
| 8 | 198 | 53.21 | 46.79 | 80.59 | 19.41 | 0.308 | 0.619 | 2.0 | 3.65 |
| 9 | 200 | 63.85 | 36.15 | 83.9 | 16.1 | 0.408 | 0.671 | 2.4 | 2.95 |
| 10 | 199 | 56.63 | 43.37 | 80.4 | 19.6 | 0.338 | 0.616 | 2.1 | 3.14 |
| 11 | 198 | 46.32 | 53.68 | 75.7 | 24.3 | 0.252 | 0.549 | 1.8 | 3.61 |
| 12 | 197 | 36.24 | 63.76 | 71.1 | 28.9 | 0.182 | 0.490 | 1.4 | 4.33 |
| 13 | 198 | 27.98 | 72.02 | 65.9 | 34.1 | 0.132 | 0.430 | 1.1 | 4.97 |
| 14 | 199 | 21.69 | 78.31 | 62.8 | 37.2 | 0.098 | 0.397 | 0.9 | 6.10 |

Notes:
(1) Operating pressures: 14.5 psia.
(2) All compositions are given on solvent-free basis.

TABLE II

EQUILIBRIUM DATA FOR ETHANOL-WATER-TRIETHYLENE GLYCOL MIXTURES

| Run No. | Temp (°F.) | Wt. % Ethanol in Liquid | Wt. % H$_2$O in Liquid | Wt. % Ethanol in Vapor | Wt. % H$_2$O in Vapor | M.F. Ethanol in Liquid | M.F. Ethanol in Vapor | Solvent to Ethanol-H$_2$O Wt. Ratio | Relative Volatility (α-ethanol/H$_2$O) |
|---|---|---|---|---|---|---|---|---|---|
| 15 | 210 | 99.40 | 0.60 | 99.68 | 0.32 | 0.984 | 0.992 | 3.5 | 1.88 |
| 16 | 209 | 95.62 | 4.38 | 97.89 | 2.11 | 0.895 | 0.948 | 3.4 | 2.13 |
| 17 | 210 | 92.19 | 7.81 | 96.36 | 3.64 | 0.822 | 0.912 | 3.3 | 2.24 |
| 18 | 208 | 87.65 | 12.35 | 94.17 | 5.83 | 0.735 | 0.863 | 3.2 | 2.28 |
| 19 | 206 | 83.48 | 16.52 | 89.50 | 10.50 | 0.664 | 0.769 | 3.1 | 1.69 |
| 20 | 205 | 77.48 | 22.52 | 88.80 | 11.20 | 0.574 | 0.756 | 2.9 | 2.30 |
| 21 | 203 | 67.76 | 32.24 | 84.88 | 15.12 | 0.451 | 0.687 | 2.5 | 2.67 |
| 22 | 200 | 54.13 | 45.87 | 79.10 | 20.90 | 0.316 | 0.597 | 2.0 | 3.21 |

Notes:
(1) Operating pressure: 14.4 psia.
(2) All compositions are given on solvent-free basis.

TABLE III

EQUILIBRIUM DATA FOR ETHANOL-WATER-TRIMETHYLENE GLYCOL MIXTURES

| Run No. | Temp (°F.) | Wt. % Ethanol in Liquid | Wt. % H$_2$O in Liquid | Wt. % Ethanol in Vapor | Wt. % H$_2$O in Vapor | M.F. Ethanol in Liquid | M.F. Ethanol in Vapor | Solvent to Ethanol-H$_2$O Wt. Ratio | Relative Volatility (α-ethanol/H$_2$O) |
|---|---|---|---|---|---|---|---|---|---|
| 23 | 226 | 98.42 | 1.58 | 99.17 | 0.83 | 0.961 | 0.979 | 3.5 | 1.92 |
| 24 | 223 | 92.11 | 7.89 | 95.80 | 4.20 | 0.820 | 0.899 | 3.3 | 1.95 |
| 25 | 222 | 88.81 | 11.19 | 94.10 | 5.90 | 0.756 | 0.862 | 3.2 | 2.01 |
| 26 | 221 | 84.62 | 15.38 | 91.70 | 8.30 | 0.683 | 0.812 | 3.1 | 2.01 |
| 27 | 219 | 78.98 | 21.02 | 89.20 | 10.80 | 0.595 | 0.764 | 2.9 | 2.20 |
| 28 | 215 | 69.08 | 30.92 | 84.30 | 15.70 | 0.466 | 0.678 | 2.6 | 2.40 |
| 29 | 211 | 55.04 | 44.96 | 77.80 | 22.20 | 0.324 | 0.578 | 2.1 | 2.86 |

Notes:
(1) Operating Pressure: 14.4 psia.
(2) All compositions are given on solvent-free basis.

TABLE IV

EQUILIBRIUM DATA FOR ETHANOL-WATER-DIETHYLENE GLYCOL MIXTURES

| Run No. | Temp (°F.) | Wt. % Ethanol in Liquid | Wt. % H$_2$O in Liquid | Wt. % Ethanol in Vapor | Wt. % H$_2$O in Vapor | M.F. Ethanol in Liquid | M.F. Ethanol in Vapor | Solvent to Ethanol-H$_2$O Wt. Ratio | Relative Volatility (α-ethanol/H$_2$O) |
|---|---|---|---|---|---|---|---|---|---|
| 30 | 217 | 99.14 | 0.86 | 99.49 | 0.51 | 97.83 | 98.70 | 3.5 | 1.69 |
| 31 | 215 | 95.55 | 4.45 | 97.87 | 2.13 | 89.35 | 94.72 | 3.4 | 2.14 |
| 32 | 214 | 92.19 | 7.81 | 96.32 | 3.68 | 82.18 | 91.09 | 3.3 | 2.22 |
| 33 | 213 | 87.65 | 12.35 | 94.15 | 5.85 | 73.50 | 86.28 | 3.2 | 2.27 |
| 34 | 212 | 83.79 | 16.21 | 92.38 | 7.62 | 66.88 | 82.57 | 3.1 | 2.35 |
| 35 | 210 | 77.78 | 22.22 | 89.40 | 10.60 | 57.76 | 76.72 | 2.9 | 2.41 |
| 36 | 208 | 68.04 | 31.96 | 85.20 | 14.80 | 45.41 | 69.22 | 2.5 | 2.70 |
| 37 | 204 | 54.24 | 45.76 | 78.60 | 21.40 | 31.65 | 58.93 | 2.0 | 3.10 |

Notes:
(1) Operating pressure: 14.2 psia.
(2) All compositions are given on solvent-free basis.

TABLE V

EQUILIBRIUM DATA FOR ETHANOL-WATER-ETHYLENE GLYCOL MIXTURES

| Run No. | Temp (°F.) | Wt. % Ethanol in Liquid | Wt. % H$_2$O in Liquid | Wt. % Ethanol in Vapor | Wt. % H$_2$O in Vapor | M.F. Ethanol in Liquid | M.F. Ethanol in Vapor | Solvent to Ethanol-H$_2$O Wt. Ratio | Relative Volatility (α-ethanol/H$_2$O) |
|---|---|---|---|---|---|---|---|---|---|
| 38 | 224 | 99.18 | 0.82 | 99.51 | 0.49 | 0.979 | 0.988 | 3.5 | 1.68 |
| 39 | 223 | 95.31 | 4.69 | 98.38 | 1.62 | 0.888 | 0.960 | 3.4 | 2.99 |
| 40 | 220 | 91.64 | 8.36 | 97.19 | 2.81 | 0.811 | 0.931 | 3.3 | 3.16 |
| 41 | 219 | 86.83 | 13.17 | 95.39 | 4.61 | 0.720 | 0.890 | 3.2 | 3.14 |
| 42 | 218 | 81.16 | 18.84 | 93.57 | 6.43 | 0.627 | 0.850 | 3.0 | 3.34 |
| 43 | 216 | 75.14 | 24.86 | 91.87 | 8.13 | 0.541 | 0.815 | 2.8 | 3.74 |
| 44 | 213 | 65.75 | 34.25 | 87.80 | 12.20 | 0.429 | 0.738 | 2.5 | 3.75 |
| 45 | 210 | 52.53 | 47.44 | 82.72 | 17.28 | 0.302 | 0.652 | 2.0 | 4.32 |

Notes:
(1) Operating pressure: 14.5 psia.
(2) All compositions are given on solvent-free basis.

TABLE VI

EQUILIBRIUM DATA FOR ETHANOL-WATER-1,4-BUTANEDIOL MIXTURES

| Run No. | Temp (°F.) | Wt. % Ethanol in Liquid | Wt. % H$_2$O in Liquid | Wt. % Ethanol in Vapor | Wt. % H$_2$O in Vapor | M.F. Ethanol in Liquid | M.F. Ethanol in Vapor | Solvent to Ethanol-H$_2$O Wt. Ratio | Relative Volatility (α-ethanol/H$_2$O) |
|---|---|---|---|---|---|---|---|---|---|
| 46 | 221 | 97.25 | 2.75 | 98.09 | 1.91 | 93.25 | 95.25 | 3.4 | 1.45 |

TABLE VI-continued

EQUILIBRIUM DATA FOR ETHANOL-WATER-1,4-BUTANEDIOL MIXTURES

| Run No. | Temp (°F.) | Wt. % Ethanol in Liquid | Wt. % $H_2O$ in Liquid | Wt. % Ethanol in Vapor | Wt. % $H_2O$ in Vapor | M.F. Ethanol in Liquid | M.F. Ethanol in Vapor | Solvent to Ethanol-$H_2O$ Wt. Ratio | Relative Volatility ($\alpha$-ethanol/$H_2O$) |
|---|---|---|---|---|---|---|---|---|---|
| 47 | 218 | 93.83 | 6.17 | 96.15 | 3.85 | 85.59 | 90.70 | 3.3 | 1.64 |
| 48 | 218 | 90.57 | 9.43 | 94.32 | 5.68 | 78.96 | 86.65 | 3.2 | 1.73 |
| 49 | 216 | 86.02 | 13.98 | 91.20 | 8.80 | 70.62 | 80.19 | 3.1 | 1.68 |
| 50 | 216 | 81.98 | 18.02 | 89.10 | 10.90 | 64.00 | 76.16 | 3.0 | 1.80 |
| 51 | 213 | 76.15 | 23.85 | 85.70 | 14.30 | 55.51 | 70.07 | 2.8 | 1.88 |
| 52 | 210 | 66.71 | 33.29 | 81.70 | 18.90 | 43.91 | 62.64 | 2.5 | 2.14 |
| 53 | 206 | 53.43 | 46.57 | 73.40 | 26.60 | 28.09 | 51.88 | 2.0 | 2.41 |

Notes:
(1) Operating Pressure: 14.4 psia.
(2) All compositions are given on solvent-free basis.

TABLE VII

EQUILIBRIUM DATA FOR ETHANOL-WATER-GLYCERIN MIXTURES

| Run No. | Temp (°F.) | Wt. % Ethanol in Liquid | Wt. % $H_2O$ in Liquid | Wt. % Ethanol in Vapor | Wt. % $H_2O$ in Vapor | M.F. Ethanol in Liquid | M.F. Ethanol in Vapor | Solvent to Ethanol-$H_2O$ Wt. Ratio | Relative Volatility ($\alpha$-ethanol/$H_2O$) |
|---|---|---|---|---|---|---|---|---|---|
| 54 | 200 | 96.75 | 3.25 | 98.97 | 1.03 | 92.09 | 97.41 | 3.4 | 3.23 |
| 55 | 200 | 93.37 | 6.63 | 98.17 | 1.83 | 84.64 | 95.45 | 3.3 | 3.81 |
| 56 | 200 | 90.18 | 9.82 | 97.44 | 2.56 | 78.23 | 93.71 | 3.2 | 4.14 |
| 57 | 200 | 85.75 | 14.25 | 96.33 | 3.67 | 70.19 | 91.13 | 3.1 | 4.36 |
| 58 | 199 | 81.61 | 18.39 | 94.94 | 5.06 | 63.46 | 88.01 | 3.0 | 4.23 |
| 59 | 198 | 75.83 | 24.17 | 93.45 | 6.55 | 55.11 | 84.81 | 2.8 | 4.55 |
| 60 | 197 | 66.34 | 33.66 | 90.38 | 9.62 | 43.54 | 78.62 | 2.5 | 4.77 |
| 61 | 196 | 53.11 | 46.89 | 86.11 | 13.89 | 30.71 | 70.81 | 2.0 | 5.47 |

Notes:
(1) Operating pressure: 14.4 psia.
(2) All compositions are given on solvent-free basis.

TABLE VIII

EQUILIBRIUM DATA FOR ETHANOL-WATER-SULFOLANE MIXTURES

| Run No. | Temp (°F.) | Wt. % Ethanol in Liquid | Wt. % $H_2O$ in Liquid | Wt. % Ethanol in Vapor | Wt. % $H_2O$ in Vapor | M.F. Ethanol in Liquid | M.F. Ethanol in Vapor | Solvent to Ethanol-$H_2O$ Wt. Ratio | Relative Volatility ($\alpha$-ethanol/$H_2O$) |
|---|---|---|---|---|---|---|---|---|---|
| 62 | 182 | 96.4 | 3.6 | 97.2 | 2.8 | 0.913 | 0.931 | 1.0 | 1.30 |
| 63 | 182 | 91.9 | 8.1 | 94.9 | 5.1 | 0.816 | 0.879 | 1.0 | 1.64 |
| 64 | 182 | 87.8 | 12.2 | 91.8 | 8.2 | 0.738 | 0.814 | 1.0 | 1.56 |
| 65 | 183 | 83.8 | 16.2 | 89.2 | 10.8 | 0.669 | 0.763 | 1.0 | 1.60 |
| 66 | 183 | 80.3 | 19.7 | 87.9 | 12.1 | 0.614 | 0.739 | 1.0 | 1.78 |
| 67 | 184 | 77.1 | 22.9 | 88.7 | 11.3 | 0.568 | 0.754 | 1.0 | 2.33 |
| 68 | 197 | 97.8 | 2.2 | 98.7 | 1.3 | 0.945 | 0.967 | 3.5 | 1.71 |
| 69 | 197 | 94.3 | 5.7 | 96.9 | 3.1 | 0.866 | 0.924 | 3.4 | 1.89 |
| 70 | 196 | 90.8 | 9.2 | 95.0 | 5.0 | 0.794 | 0.881 | 3.3 | 1.93 |
| 71 | 196 | 86.4 | 13.6 | 93.1 | 6.9 | 0.712 | 0.841 | 3.1 | 2.12 |
| 72 | 195 | 80.4 | 19.6 | 89.3 | 10.7 | 0.616 | 0.765 | 3.0 | 2.03 |
| 73 | 195 | 74.8 | 25.2 | 86.6 | 13.4 | 0.537 | 0.716 | 2.8 | 2.18 |
| 74 | 195 | 65.9 | 34.1 | 82.7 | 17.3 | 0.430 | 0.651 | 2.5 | 2.47 |
| 75 | 195 | 52.7 | 47.3 | 77.7 | 22.3 | 0.303 | 0.577 | 2.0 | 3.13 |

Notes:
(1) Operating pressure: 14.5 psia.
(2) All compositions are given on solvent-free basis.

TABLE IX

EQUILIBRIUM DATA FOR ETHANOL-WATER-N—METHYL-PYRROLIDONE MIXTURES

| Run No. | Temp (°F.) | Wt. % Ethanol in Liquid | Wt. % $H_2O$ in Liquid | Wt. % Ethanol in Vapor | Wt. % $H_2O$ in Vapor | M.F. Ethanol in Liquid | M.F. Ethanol in Vapor | Solvent to Ethanol-$H_2O$ Wt. Ratio | Relative Volatility ($\alpha$-ethanol/$H_2O$) |
|---|---|---|---|---|---|---|---|---|---|
| 76 | 239 | 99.13 | 0.87 | 99.33 | 0.67 | 0.978 | 0.983 | 3.5 | 1.30 |
| 77 | 236 | 95.34 | 4.66 | 96.88 | 3.12 | 0.889 | 0.924 | 3.4 | 1.52 |
| 78 | 233 | 91.40 | 8.60 | 94.64 | 5.36 | 0.806 | 0.873 | 3.3 | 1.66 |
| 79 | 230 | 86.63 | 13.37 | 92.32 | 7.68 | 0.717 | 0.824 | 3.2 | 1.86 |
| 80 | 226 | 81.09 | 18.91 | 88.23 | 11.77 | 0.626 | 0.745 | 3.0 | 1.75 |
| 81 | 223 | 75.18 | 24.82 | 85.35 | 14.65 | 0.542 | 0.695 | 2.8 | 1.92 |
| 82 | 218 | 65.76 | 34.24 | 81.28 | 18.72 | 0.429 | 0.629 | 2.5 | 2.26 |
| 83 | 212 | 52.15 | 47.85 | 74.10 | 25.90 | 0.299 | 0.528 | 2.0 | 2.63 |

Notes:
(1) Operating pressure: 14.4 psia.
(2) All compositions are given on solvent-free basis.

TABLE X
EQUILIBRIUM DATA FOR ETHANOL-WATER-PHENYLTHIOETHANOL MIXTURES

| Run No. | Temp (°F.) | Wt. % Ethanol in Liquid | Wt. % H$_2$O in Liquid | Wt. % Ethanol in Vapor | Wt. % H$_2$O in Vapor | M.F. Ethanol in Liquid | M.F. Ethanol in Vapor | Solvent to Ethanol-H$_2$O Wt. Ratio | Relative Volatility ($\alpha$-ethanol/H$_2$O) |
|---|---|---|---|---|---|---|---|---|---|
| 84 | 200 | 99.17 | 0.83 | 99.44 | 0.56 | 0.979 | 0.986 | 3.5 | 1.49 |
| 85 | 200 | 98.11 | 1.89 | 98.44 | 1.56 | 0.953 | 0.961 | 3.5 | 1.22 |
| 86 | 197 | 94.33 | 5.67 | 95.35 | 4.65 | 0.867 | 0.889 | 3.4 | 1.23 |
| 87 | 195 | 89.94 | 10.56 | 91.77 | 8.23 | 0.769 | 0.813 | 3.2 | 1.31 |
| 88 | 193 | 82.77 | 17.23 | 87.17 | 12.83 | 0.652 | 0.726 | 3.0 | 1.41 |
| 89 | 192 | 77.08 | 22.92 | 80.64 | 19.36 | 0.568 | 0.619 | 2.8 | 1.24 |
| 90 | 191 | 67.59 | 32.41 | 74.78 | 25.22 | 0.449 | 0.537 | 2.5 | 1.42 |
| 91 | 191 | 54.15 | 45.85 | 68.84 | 31.16 | 0.316 | 0.463 | 2.0 | 1.87 |

Notes:
(1) Operating pressure: 14.5 psia.
(2) All Compositions are given on solvent-free basis.

TABLE XI
EQUILIBRIUM DATA FOR ETHANOL-WATER-DI-n-PROPYL SULFONE MIXTURES

| Run No. | Temp (°F.) | Wt. % Ethanol in Liquid | Wt. % H$_2$O in Liquid | Wt. % Ethanol in Vapor | Wt. % H$_2$O in Vapor | M.F. Ethanol in Liquid | M.F. Ethanol in Vapor | Solvent to Ethanol-H$_2$O Wt. Ratio | Relative Volatility ($\alpha$-ethaol/H$_2$O) |
|---|---|---|---|---|---|---|---|---|---|
| 92 | 203 | 99.60 | 0.40 | 99.49 | 0.51 | 0.990 | 0.987 | 3.5 | 0.78 |
| 93 | 202 | 98.67 | 1.33 | 99.43 | 0.57 | 0.967 | 0.986 | 3.5 | 2.35 |
| 94 | 201 | 95.05 | 4.95 | 95.74 | 4.26 | 0.882 | 0.898 | 3.4 | 1.17 |
| 95 | 199 | 90.14 | 9.86 | 91.88 | 8.12 | 0.781 | 0.816 | 3.3 | 1.24 |
| 96 | 197 | 83.35 | 16.65 | 87.04 | 12.96 | 0.662 | 0.724 | 3.0 | 1.34 |
| 97 | 195 | 77.08 | 22.92 | 82.50 | 17.50 | 0.568 | 0.648 | 2.8 | 1.40 |
| 98 | 194 | 67.59 | 32.41 | 77.89 | 22.11 | 0.449 | 0.579 | 2.5 | 1.69 |
| 99 | 194 | 54.27 | 45.73 | 70.37 | 29.63 | 0.317 | 0.481 | 2.0 | 2.00 |

Notes:
(1) Operating pressure: 14.5 psia.
(2) All compositions are given on solvent-free basis.

Figure 3:
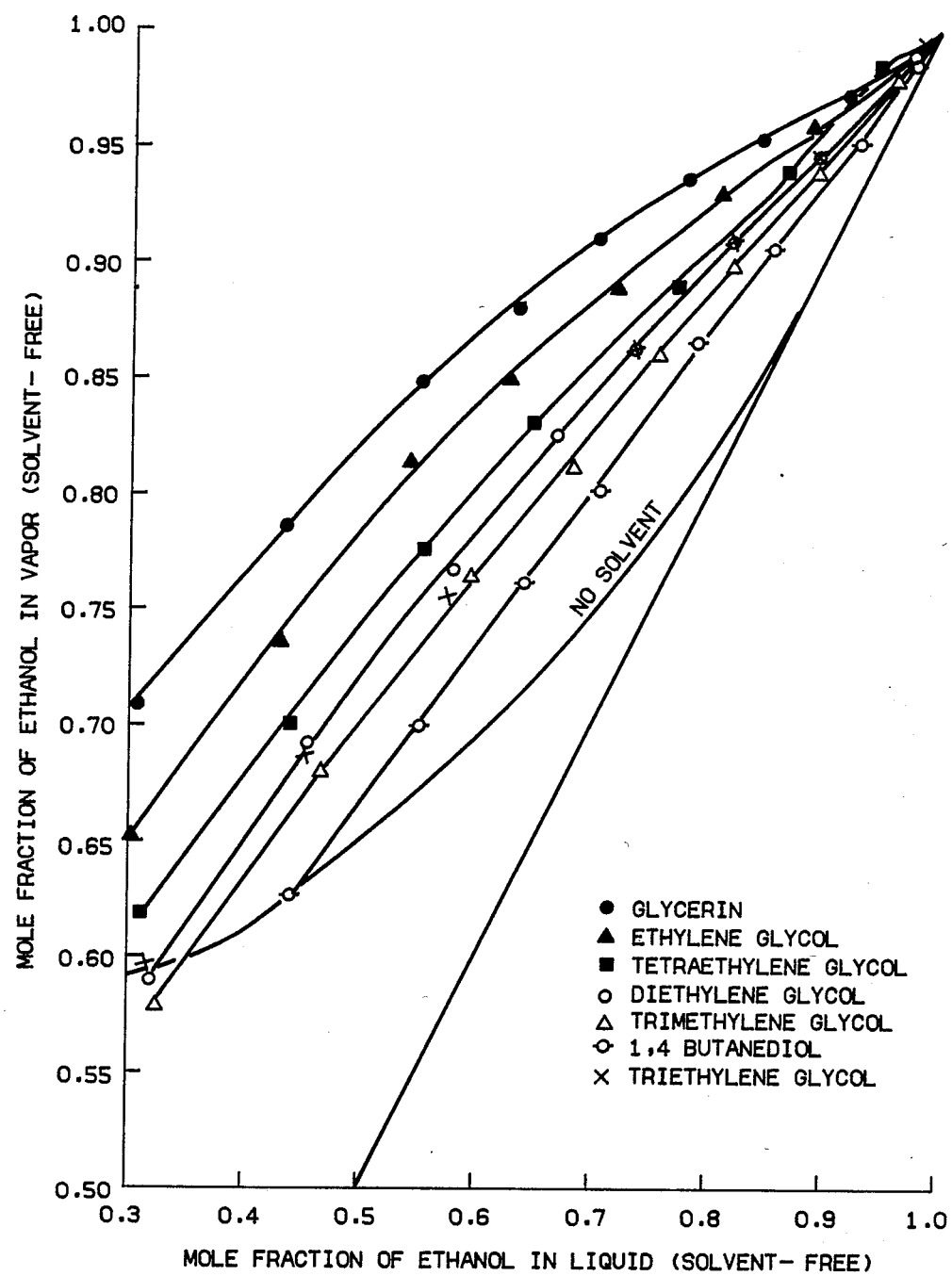
FIG. 3 is a graphical representation of the pseudo-binary vapor-liquid equilibrium (VLE) relationships of an ethanol-water system illustrating the effects of the use of seven extractive solvents in comparison with the use of no solvent.

From the relative volatilities ($\alpha_{12}$) presented in the foregoing data, it will be seen that the glycols are more selective than other organic solvents with glycerin being the most selective solvent. FIG. 3 summarizes the ethanol-rich portion of the pseudo-binary VLE curves for all the tested glycols for comparison. It will be seen that the addition of the glycols as solvents breaks the ethanol-water azeotrope and changes the VLE curve favorably for distillation. The selectivity of these solvents is proportional to the number of hydroxyl groups on the molecule and inversely proportional to the carbon chain length of the molecule. Also, the solvent selectivity is enhanced by the existence of oxygen in the carbon chain.

The operating temperature varied from about 198° F. (92° C.) to about 226° F. (108° C.) for the runs with the glycols as solvents, but the temperature variation is considered to be insignificant because the $\alpha_{12}$ values change only slightly with temperature. Since the operating pressure was kept essentially constant, it is considered that the recorded changes in $\alpha_{12}$ values are caused only by the composition of the mixtures.

It should be pointed out that for each solvent screened, the runs were carried out under different solvent to ethanol-water ratios (S/F) with the highest ratio at the highest ethanol concentration as shown in Tables I through XI. The S/F ratio values were decreased gradually with decreasing ethanol concentration. Normally, the higher the S/F ratio, the higher the relative volatility $\alpha_{12}$. This is not true, however, for ethanol-water mixtures where the strong dependency of $\alpha_{12}$ on S/F ratio was only observed at high ethanol concentration (above the concentration of ethanol-water azeotrope). At lower ethanol concentration, however, the value of $\alpha_{12}$ is dependent of the S/F ratio and the data points can be fitted on a single curve regardless of the S/F ratio value. An example of these observations is given in FIG. 4 which depicts a pseudo-binary vapor-liquid equilibrium curve for the ethanol-water-ethylene glycol system.

Figure 4:
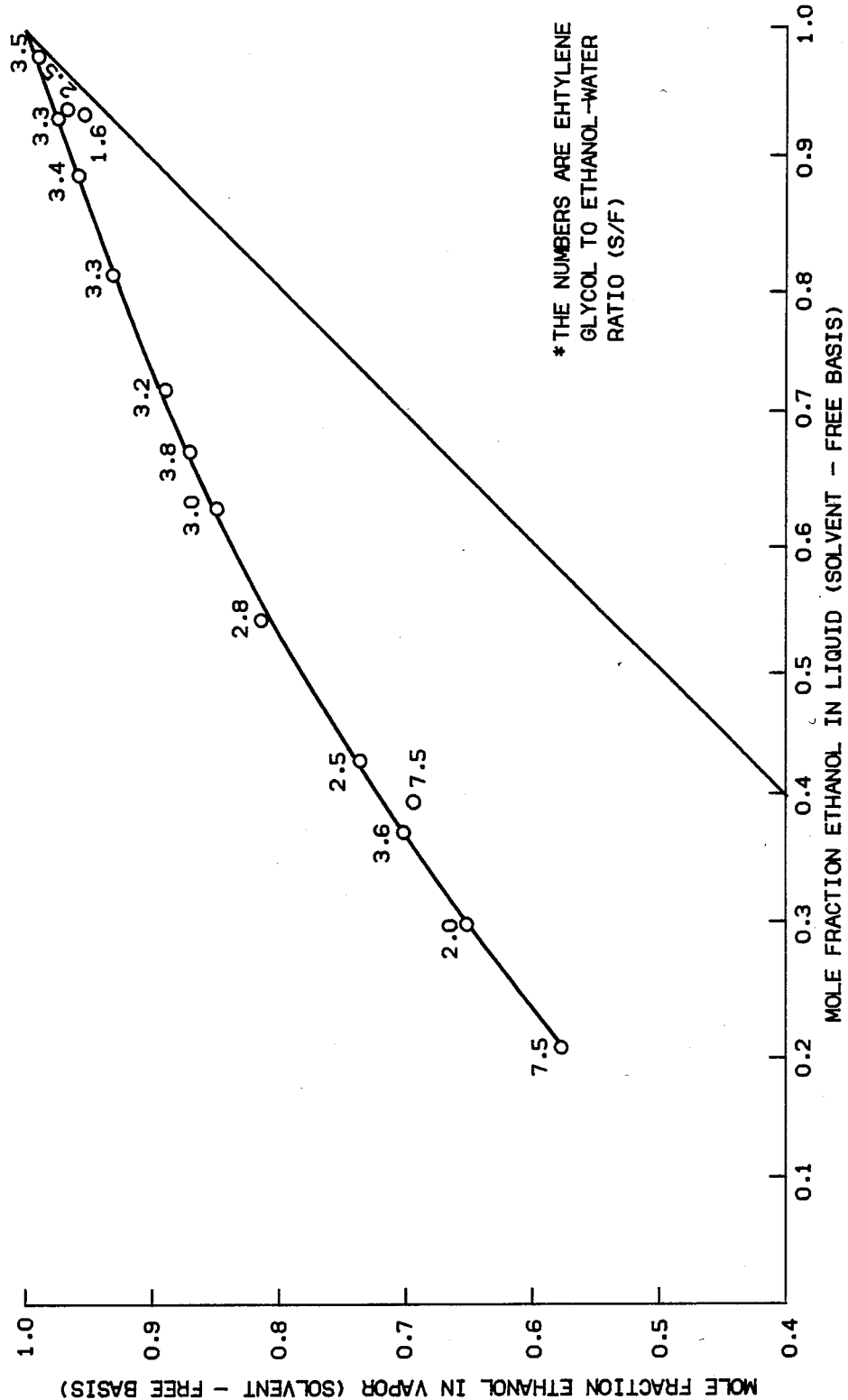
FIG. 4 is a graphical representation of the pseudo-binary VLE relationships of an ethanol-water-ethylene glycol system.

The process of the present invention is directed to an improved extractive distillation process for producing anhydrous ethanol and is based on the foregoing analysis of the solvent screening data presented in Tables I through XI and FIGS. 3 and 4. A system for forming the process of the present invention is depicted in the schematic process diagram of FIG. 5 and is generally designated by the reference character 10.

In the extractive distillation process of the present invention, extractive solvent is added only to the ethanol-rich portion of the fractionator where the VLE curve is very unfavorable for distillation. As previously indicated, the addition of a solvent such as the glycols and others screened in Example I not only eliminates the ethanol-water azeotrope, but changes the shape of the ethanol-rich portion of the VLE curves favorably for distillation. The ethanol-water saturated solvent is then completely removed from the fractionator and fed to a suitable solvent stripper. Only the overhead vapor from the solvent stripper is transferred to the lower or ethanol-lean portion of the fractionator where no solvent is needed.

Figure 5:
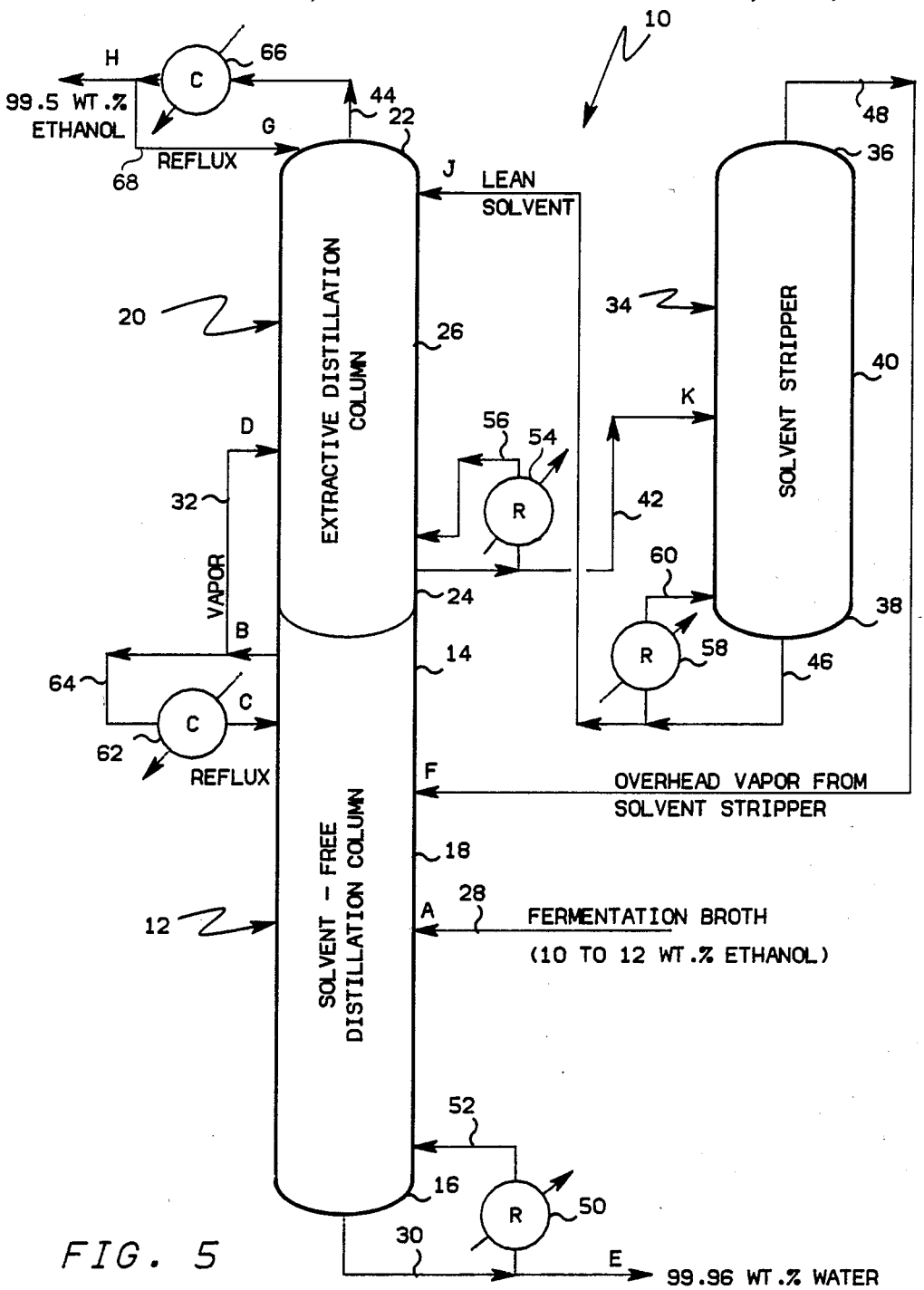
FIG. 5 is a schematic diagram depicting the process of the invention.

Referring now to FIG. 5, the system 10 comprises a first distillation column 12 having an upper portion 14, a lower portion 16 and a medial portion 18, and defining a first distillation zone. The system 10 is further provided with a second or extractive distillation column 20 having an upper portion 22, a lower portion 24 and a medial portion 26, and defining an extractive distillation zone. The distillation columns 12 and 20 can be located separately from one another or the extractive distillation column 20 can be located directly above and coaxially aligned with the first distillation column 12 as specifically depicted in FIG. 5. A first conduit 28 is in fluid flow communication between the medial portion of the interior of the first distillation column 12 and a suitable source of feedstock, such as a fermentation broth, containing ethanol. A suitable feedstock can be an aqueous solution containing ethanol in the range from about 10 to about 12 weight percent based on the total weight of the feedstock. A second conduit 30 is in fluid flow communication with the lower portion of the interior of the first distillation column 12 and provides means for conveying a stream of liquid bottoms comprising water from the first distillation column 12. A third conduit 32 is in fluid flow communication between the upper portion of the interior of the first distillation column 12 and the medial portion of the interior of the extractive distillation column 20 and provides means for conveying a stream of vapor overhead comprising ethanol from the first distillation column 12 to the extractive distillation column 20.

The system 10 further includes a third distillation column or other suitable solvent stripper 34 having an upper portion 36, a lower portion 38 and a medial portion 40, and defining a solvent stripper zone. A fourth conduit 42 is connected in fluid flow communication between the lower portion of the interior of the extractive distillation column 20 and the medial portion of the interior of the solvent stripper 34 and provides means for conveying a stream of fluid bottoms from the extractive distillation column 20 to the solvent stripper 34. A fifth conduit 44 is connected in fluid flow communication with the upper portion of the interior of the extractive distillation column 20 and provides means for conveying a stream of vapor overhead comprising anhydrous ethanol from the extractive distillation column 20.

A sixth conduit 46 is connected in fluid flow communication between the lower portion of the interior of the solvent stripper 34 and the upper portion of the interior of the extractive distillation column 20 and provides means for conveying a stream of lean solvent from the lower portion of the solvent stripper 34 into the upper portion of the interior of the extractive distillation column 20. A seventh conduit 48 is connected in fluid flow communication between the interior of the upper portion of the solvent stripper 34 and the interior of the medial portion of the first distillation column 12 and provides means for conveying water and ethanol vapor overhead from the solvent stripper 34 to the interior of the first distillation column 12.

A first reboiler 50 is interposed in a conduit 52 which is connected in fluid flow communication between second conduit 30 and the lower portion of the interior of the first distillation column 12. A second reboiler 54 is interposed in a conduit 56 which is connected in fluid flow communication between the fourth conduit 42 and the lower portion of the interior of the extractive distillation column 20. A third reboiler 58 is interposed in a conduit 60 which is connected in fluid flow communication between conduit 46 and the lower portion of the interior of the solvent stripper 34.

A first condenser 62 is interposed in conduit 64 which is connected in fluid flow communication between third conduit 32 and the upper portion of the interior of the first distillation column 12 to provide a reflux stream to the first distillation column 12. A second condenser 66 is interposed in the fifth conduit 44, and a conduit 68 is connected in fluid flow communication between the conduit 44 downstream of the second condenser 66 and the upper portion of the interior of the extractive distillation column 20 to provide a reflux stream of condensed ethanol to the upper portion of the interior of the extractive distillation column.

The following is a calculated example illustrating the operation of the process and apparatus of the present invention.

EXAMPLE II

Figure 6:
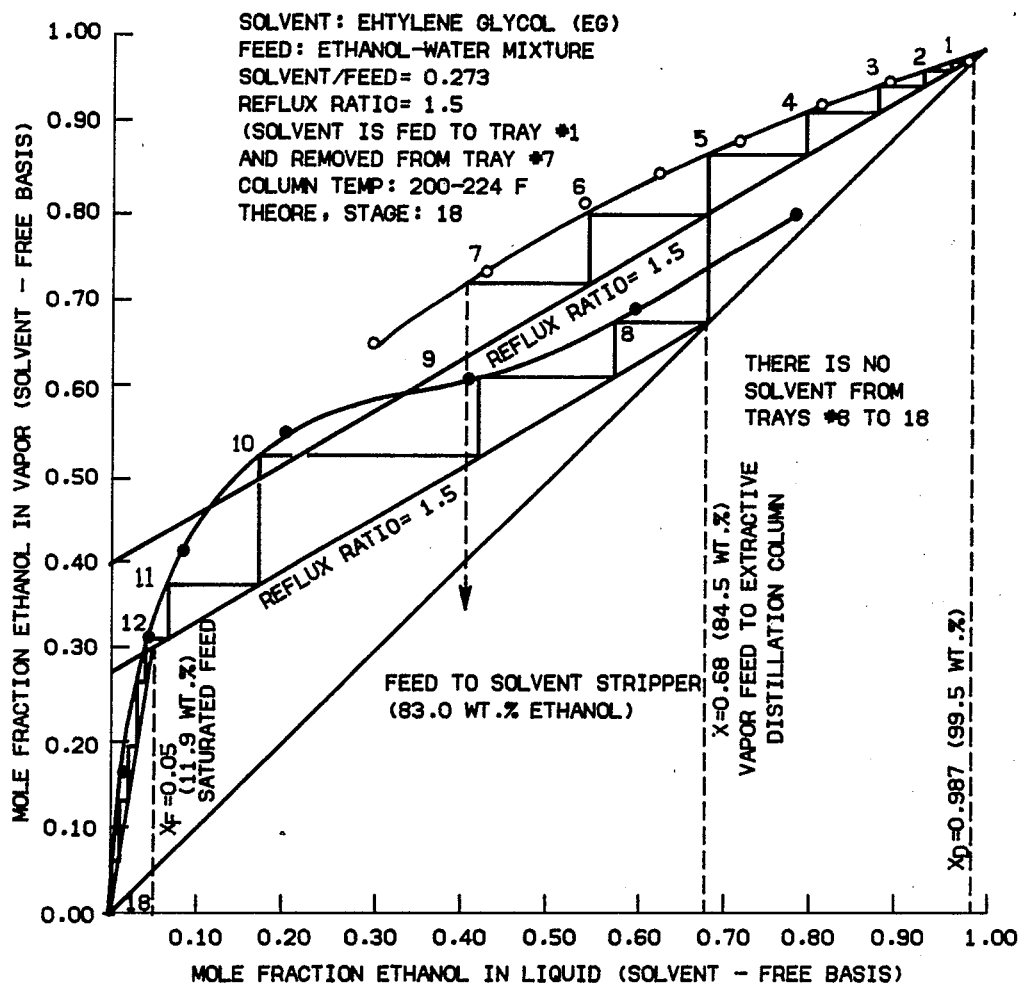
FIG. 6 is a graphical representation of the McCabe-Thiele relationship applied to the VLE curve of an ethanol-water-ethylene glycol system.

In this example ethylene glycol is used as the extractive distillation solvent for recovering dehydrated ethanol of 99.5 weight percent ethanol from a fermentation broth containing 11.9 weight percent ethanol. As shown in FIG. 6, the McCabe-Thiele graphical design procedures are performed on the VLE curves based on the data from Table V. According to FIG. 6, the fermentation broth near its bubble point should be fed to distillation column 12 (the solvent-free portion) of the fractionator on tray number 12. It will be noted that eighteen theoretical trays are employed in distillation columns 12 and 20 with trays 1 through 7 being numbered consecutively from top to bottom in the extractive distillation column 20 and with trays 8 through 18 being numbered consecutively from top to bottom in the first distillation column 12. Part of the overhead vapor from the first distillation column 12 is introduced as the concentrated feed to the extractive distillation column 20 at tray number 5 via conduit 32 as shown in FIG. 5. The other portion of the overhead vapor from the first distillation column 12 is condensed and recycled as the reflux to the first distillation column on tray number 8 via conduit 64 and condenser 62. The bottom product of the first distillation column 12 containing 99.99 mole percent water is removed via conduit 30. A portion of this bottom product is recycled via reboiler 50 and conduit 52 with the remainder being recycled to the fermenter (not shown).

Lean ethylene glycol solvent is fed near the top of the extractive distillation column 20 via conduit 46 at about 20° F. below the column temperature to generate internal reflux and improve the solvent selectivity (the lower the temperature, the higher the solvent selectivity). The ethylene glycol solvent enhances the relative volatility and improves the VLE curve of the ethanol-water mixture, allowing separation of the feed into an overhead stream of dehydrated ethanol of 98.7 mole percent (99.5 weight percent) ethanol and a bottom-rich solvent stream of 40.5 mole percent ethanol (on solvent-free basis). The overhead stream from the extractive distillation column exits via conduit 44 and condenser 66 with about 60 percent of the overhead stream recycled as the reflux to the extractive distillation column 20 via conduit 68. The bottom stream from the extractive distillation column 20 is transferred to the solvent stripper 34 via conduit 42 with a portion thereof recycled via reboiler 54 and conduit 56 to tray number 7 of the extractive distillation column 20.

The operating conditions in the solvent stripper 34, including temperature and pressure, cause the rich solvent received from conduit 42 to separate into an overhead stream containing only ethanol and water and a bottom stream containing essentially dry lean solvent, in this case ethylene glycol. The overhead stream from the solvent striper 34 is fed via conduit 48 to tray number 10 of the solvent-free first distillation column 12, while the bottom stream is conducted via conduit 46 as the lean ethylene glycol solvent feed to tray number 1 of the extractive distillation column 20. The flow rate and composition of all the streams, A through H, J and K, of this extractive distillation process are summarized in Table XII.

TABLE XII

PROCESS FLOW RATES AND COMPOSITIONS OF THE EXTRACTIVE DISTILLATION PROCESS

Basis: 100 lb-mole/hr fermentation broth as the feed
27.3 lb-mole/hr ethylene glycol as the solvent

| Stream Reference Letter* | Flow Rate (lb-mole/hr) | Ethanol Composition** | | Tray No. (From the Top) *** | Stream Descriptions |
|---|---|---|---|---|---|
| | | Mole Fraction | Wt. % | | |
| A | 100.0 | 0.051 | 11.9 | 12 | Ethanol Feed (Fermentation Broth) |
| B | 27.5 | 0.680 | 84.5 | 8 | Overhead Vapor from Column 12 |
| C | 16.5 | 0.680 | 84.5 | 8 | Reflux of Column 12 |
| D | 11.0 | 0.680 | 84.5 | 5 | Vapor Feed to Column 20 |
| E | 94.8 | 0.0001 | 0.03 | 18 | Bottom Product from Column 12 |
| F | 5.8 | 0.405 | 63.0 | 10 | Overhead Vapor from Stripper to Column 12 |
| G | 7.8 | 0.987 | 99.5 | 1 | Reflux of Column 20 |
| H | 5.2 | 0.987 | 99.5 | 1 | Overhead Product of Column 20 |
| J | 27.3 | 0.000 | 0.0 | 1 | Lean Solvent to Column 20 |
| K | 33.1 | 0.405 | 63.0 | 7 | Bottom Stream of Column 20 Stripper 34 |

*Refer to FIG. 5.
**Ethanol Compositions are on Solvent-Free Basis.
***Number of Theroetical Trays.

From the foregoing Example II, the following advantages of the process described therein are as follows. With a suitable solvent, such as ethylene glycol, anhydrous ethanol can be produced from the fermentation broth in a column with eighteen theoretical trays. A low reflux ratio, such as 1.5, is needed for the separation, thus cutting down energy and investment costs. A low solvent-to-feed ratio, such as 0.27 (based on fermentation broth), is required by the process. Only minor changes and low capital investment would be necessary to convert an existing distillation plant into a plant capable of performing the low energy process of the present invention.

From the foregoing it will also be seen that the instant invention provides an integrated process in which the initial distillation ultimately rejects all the water removed in the process as kettle product, and ethanol is concentrated to a concentration in the range from about 80 to about 90 weight percent, and preferably to a concentration of from about 84 to about 86 weight percent. This overhead product is yielded from the initial step as a vapor and becomes the vapor feed to the extractive distillation step wherein the vapor is countercurrently contacted with a selective solvent to remove the remaining water from the ethanol. Any solvent which will provide the desired extractive distillation of ethanol in the process of the present invention can be employed. Such solvents include, for example, glycols such as ethylene glycol, diethylene glycol, trimethylene glycol, triethylene glycol and tetraethylene glycol, glycerin, sulfolane and 1,4-butanediol, and combinations of any two or more thereof. Best results are obtained from the employment of glycerin and/or ethylene glycol as the solvent in the process of the present invention. Rich solvent from solvent extraction passes to the solvent stripper from which the vaporous overhead product is injected into the fractionator at a suitable intermediate point and the lean solvent is returned to the extractive distillation column.

Modifications and variations of the invention as hereinbefore set forth in the specification and shown in the drawings may be made without departing from the spirit and scope of the invention as defined and limited only by the following claims.

We claim:

1. A process for dehydrating an aqueous feedstock comprising water and ethanol, comprising:
   distilling said feedstock under distillation conditions in a first distillation zone to produce a first liquid bottoms product and a first vapor overhead stream comprising ethanol and water;
   introducing at least a portion of said first vapor overhead stream into an extractive distillation zone;
   contacting said thus introduced first vapor overhead with a selective solvent in said extractive distillation zone under extractive distillation conditions to thereby produce a second liquid bottoms product comprising water and said selective solvent and to thereby produce a second vapor overhead stream comprising greater than 95.57 weight percent ethanol based on the total weight of said second vapor overhead;
   introducing at least a portion of said second liquid bottoms product comprising water and said selective solvent into a solvent stripper zone;
   separating said second bottoms product under solvent stripping conditions in said solvent stripper zone into a third vapor overhead stream comprising water and ethanol and a third liquid bottoms product comprising said selective solvent; and
   introducing at least a portion of said third vapor overhead stream into said first distillation zone.

2. A process in accordance with claim 1 wherein said solvent stripping conditions include a subatmospheric pressure.

3. A process in accordance with claim 1 wherein said solvent stripping conditions include a temperature above the boiling point of water and below the boiling point of said selective solvent.

4. A process in accordance with claim 1 wherein said selective solvent consists essentially of a composition selected from the group consisting of ethylene glycol, diethylene glycol, triethylene glycol, tetraethylene glycol, trimethylene glycol, glycerin, sulfolane, 1,4-butandediol, N-methyl pyrrolidone, phenylthioethanol, di-n-propyl sulfone, and combinations of any two or more thereof.

5. A process in accordance with claim 1 wherein said selective solvent consists essentially of ethylene glycol.

6. A process in accordance with claim 1 wherein said selective solvent consists essentially of glycerin.

7. A process in accordance with claim 1 characterized further to include:
introducing at least a portion of said third bottoms product stream into said extractive distillation zone.

8. A process in accordance with claim 7 wherein said feedstock consists essentially of fermentation broth.

9. A process in accordance with claim 1 wherein said feedstock consists essentially of fermentation broth and said selective solvent consists essentially of a composition selected from the group consisting of ethylene glycol, diethylene glycol, triethylene glycol, tetraethylene glycol, trimethylene glycol, glycerin, sulfolane, 1,4-butanediol, N-methyl pyrrolidone, phenylthioethanol, di-n-propyl sulfone, and combinations of any two or more thereof.

10. A process in accordance with claim 1 wherein said feedstock comprises no more than about 14 weight percent ethanol based on the total weight of the feedstock.

11. A process in accordance with claim 1 wherein said first vapor overhead comprises no more than about 90 weight percent ethanol based on the total weight of said first vapor overhead.

12. A process in accordance with claim 1 wherein said first vapor overhead comprises ethabol in the range from about 85 to about 90 weight percent based on the total weight of said first vapor overhead.

13. A process in accordance with claim 1 wherein said second vapor overhead comprises at least about 99 weight percent ethanol based on the total weight of said second vapor overhead.

14. A process in accordance with claim 1 wherein said second vapor overhead comprises at least about 99.5 weight percent ethanol based on the total weight of said second vapor overhead.

15. A process in accordance with claim 1 wherein said aqueous feedstock consists essentially of fermentation broth.

* * * * *